United States Patent
Michel et al.

(10) Patent No.: US 9,241,486 B2
(45) Date of Patent: Jan. 26, 2016

(54) COMBINATION AND METHODS FOR CONTROLLING TURFGRASS PESTS

(71) Applicant: Bayer CropScience LP, Research Triangle Park, NC (US)

(72) Inventors: Jeffrey A. Michel, Raleigh, NC (US); Kenneth A. Kukorowski, Raleigh, NC (US)

(73) Assignee: BAYER CROPSCIENCE LP, Research Triangle Park, NC (US)

( * ) Notice: Subject to any disclaimer, the term of this patent is extended or adjusted under 35 U.S.C. 154(b) by 109 days.

(21) Appl. No.: 13/790,375

(22) Filed: Mar. 8, 2013

(65) Prior Publication Data

US 2014/0088092 A1  Mar. 27, 2014

Related U.S. Application Data

(60) Provisional application No. 61/695,872, filed on Aug. 31, 2012.

(51) Int. Cl.

| | |
|---|---|
| *A01N 43/38* | (2006.01) |
| *A01N 43/50* | (2006.01) |
| *A01N 43/08* | (2006.01) |
| *A01N 43/40* | (2006.01) |
| *A01N 43/78* | (2006.01) |
| *A01N 43/12* | (2006.01) |
| *A01N 43/88* | (2006.01) |
| *A01N 47/06* | (2006.01) |

(52) U.S. Cl.
CPC ............... *A01N 43/40* (2013.01); *A01N 43/08* (2013.01); *A01N 43/12* (2013.01); *A01N 43/38* (2013.01); *A01N 43/50* (2013.01); *A01N 43/78* (2013.01); *A01N 43/88* (2013.01); *A01N 47/06* (2013.01)

(58) Field of Classification Search
CPC ....... A01N 43/38; A01N 43/12; A01N 43/50; A01N 43/88; A01N 43/40; A01N 43/78; A01N 43/08
USPC ............. 514/229.2, 409, 462, 341, 357, 342, 514/365
See application file for complete search history.

(56) References Cited

U.S. PATENT DOCUMENTS

| | | | |
|---|---|---|---|
| 7,897,803 B2 | 3/2011 | Himmler et al. | |
| 2009/0247597 A1 | 10/2009 | Vermeer et al. | |
| 2010/0249121 A1 | 9/2010 | Fischer et al. | |
| 2011/0177948 A1* | 7/2011 | Vermeer et al. | ............... 504/253 |
| 2011/0200571 A1 | 8/2011 | Bell et al. | |
| 2014/0163076 A1 | 6/2014 | Fischer et al. | |

FOREIGN PATENT DOCUMENTS

| | | |
|---|---|---|
| EP | 0 192 060 A1 | 8/1986 |
| EP | 0 235 725 A2 | 9/1987 |
| EP | 0 302 389 A2 | 2/1989 |
| EP | 0 376 279 A2 | 7/1990 |
| EP | 0 580 553 A2 | 1/1994 |
| EP | 0 649 845 A1 | 4/1995 |
| EP | 2 008 519 A1 | 12/2008 |
| EP | 2 011 394 A1 | 1/2009 |
| WO | 91/04965 | 4/1991 |
| WO | 2004/007448 A1 | 1/2004 |
| WO | 2008/037377 A2 | 4/2008 |
| WO | 2011/100424 A1 | 8/2011 |
| WO | 2011/134820 A1 | 11/2011 |

OTHER PUBLICATIONS

Eileen A. Buss, Southern Chinch Bug Management on St. Augustine grass, ENY-325 (LH036)—http://edis.ifas.ufl.edu, Rev. 2007.*
MERIT® 2F product sheet.*
MOVENTO® label.*
Buss "Insect Pest Management of Turfgrass" ENY-300, Jan. 1, 2009, XP055066837.
International Search Report of PCT/US2013/029749.
International Search Report of PCT/US2013/029749 Dated Sep. 7, 2013.
Notification Concerning Transmittal of International Preliminary Report on Patentability and Written Opinion of the International Searching Authority dated Mar. 3, 2015, issued in PCT/US2013/029749.

* cited by examiner

*Primary Examiner* — Sarah Pihonak
*Assistant Examiner* — Jason A Deck
(74) *Attorney, Agent, or Firm* — Miles & Stockbridge P.C.

(57) ABSTRACT

The present invention relates to the use of active substance combinations for controlling animal pests, for example, from the chinch bug family (Lygaeidae), as well as animal pests that has shown resistance to pyrethroids.

9 Claims, No Drawings

COMBINATION AND METHODS FOR
CONTROLLING TURFGRASS PESTS

CROSS REFERENCE TO RELATED APPLICATIONS

This application claims priority to U.S. Provisional Patent Application No. 61/695,872, filed under 35 U.S.C. §111(b) on Aug. 31, 2012, which is hereby incorporated by reference in its entirety.

FIELD

The present invention relates to the use of active substance combinations for controlling animal pests, for example, from the chinch bug family (Lygaeidae), as well as animal pests that have shown resistance to pyrethroids.

BACKGROUND

Many animal pests, such as insects, arachnoids, and nematodes, such as chinch bug (Family Lygaeidae) Annual bluegrass weevil (Family Curculionidae), Rhodesgrass mealybug (Family Pseudococcidae), Banks grass mite (Family Tetranychidae), Ground pearls (Family Margarodidae), 2-lined spittlebug (Family Cercopidae), Billbug (Family Curculionidae), ticks, fleas, and various root parasitic nematodes, cause problems such as, feedings that can damage or kill turfgrass. For example, chinch bugs, especially the Southern Chinch bugs (*Blissus insularis*), damages St. Augustine grass in Florida.

Pyrethroids, especially bifenthrin, organochlorines, and organophosphates have been used for many years to control the pests. As a result, the pests have developed wide-spread resistance to a number of chemical classes, including organochlorines, organophosphates, and/or pyrethroids.

While many still use pyrethroids to control these pests, they have had to apply more pyrethroids at higher rates to overcome resistance. Some pest populations are now completely uncontrolled with all labeled rates of pyrethroid chemistry. Pyrethroid resistance in chinch bugs is well documented in Florida, and turf managers are quite aware of this potential problem. This has led to a search in the industry for non-pyrethroid chemistry to use to control the pests.

SUMMARY

In an aspect, the disclosure provides for a method for controlling animal pests by applying a combination comprising nicotinic acetylcholine receptor agonist or antagonist and a ketoenol, together or separately, to turfgrass.

In an aspect, the disclosure provides for a method for controlling animal pests that have shown resistance to pyrethroids by applying a combination comprising nicotinic acetylcholine receptor agonist or antagonist and a ketoenol, together or separately, to turfgrass.

In an aspect, the disclosure provides for a method for controlling animal pests by applying a combination comprising imidacloprid and spirotetramat, together or separately, to turfgrass.

In an aspect, the disclosure provides for a method for controlling animal pests that have shown resistance to pyrethroids by applying a combination comprising imidacloprid and spirotetramat, together or separately, to turfgrass.

In an aspect, the disclosure provides for a combination comprising a nicotinic acetylcholine receptor agonist or antagonist and a ketoenol, together or separately.

In an aspect, the disclosure provides for a combination comprising imidacloprid and spirotetramat, together or separately.

In an aspect, a combination comprising nicotinic acetylcholine receptor agonist or antagonist and a ketoenol is applied to turfgrass. In another aspect, the combination is applied separately. In an aspect, a combination described herein is applied to turfgrass in an amount effective to reduce damage to the turfgrass caused by an animal pest. In an aspect, a combination described herein is applied to turfgrass in an amount effective to control an animal pest.

In an aspect, the animal pest is from the chinch bug family (Lygaeidae).

In an aspect, a combination described herein is applied to a crop at about 1-1000 grams of ketoenol per hectacre, and about 1-1000 grams of nicotinic acetylcholine receptor agonist or antagonist per hectare. In an aspect, a combination described herein is applied to a crop at about 1-500 grams of ketoenol per hectacre, and about 1-500 grams of nicotinic acetylcholine receptor agonist or antagonist per hectare. In an aspect, a combination described herein is applied to a crop at about 1-250 grams of ketoenol per hectacre, and about 100-500 grams of nicotinic acetylcholine receptor agonist or antagonist per hectare. In an aspect, a combination described herein is applied to a crop at about 100-200 grams of ketoenol per hectacre, and about 200-500 grams of nicotinic acetylcholine receptor agonist or antagonist per hectare. In an aspect, a combination described herein is applied to a crop at about 88-176 grams of ketoenol per hectacre, and about 220-450 grams of nicotinic acetylcholine receptor agonist or antagonist per hectare.

In an aspect, a combination described herein is applied sequentially, separately where either compound is applied first, together as a tank mix in a single combination, or applied together as a formulated product containing both active ingredients.

In an aspect, a combination described herein is applied as a tank mix (imidacloprid+spirotetramat), pre-mixed combination product sold in one bottle to the customer, granular formulation, granular formulation on fertilizer formulation, plant pin, or table form, imidacloprid sprayed first and spirotetromat sprayed next, or vice versa. Applications can be made through irrigation system, hose end sprayer, and ready to use sprayer.

DETAILED DESCRIPTION

In an aspect the disclosure provides for a method of controlling animal pests with a combination or composition described herein. In an aspect, the disclosure provides for a method of controlling animal pests that have shown resistance to pyrethroids by applying a combination or composition described herein to turfgrass. In an aspect, the disclosure provides for a method of treating turfgrass with a combination or composition described herein, the turgrass can be infected turfgrass or as a preventative means to those turfgrass not affected. In an aspect, the animal pest is chinch bugs (family Lygaeidae).

In an aspect, a combination described herein comprises, consists of, or consists essentially of nicotinic acetylcholine receptor agonist or antagonist and ketoenol. In an aspect, a combination described herein comprises, consists of, or consists essentially of ketoenol compounds selected from (I-1)
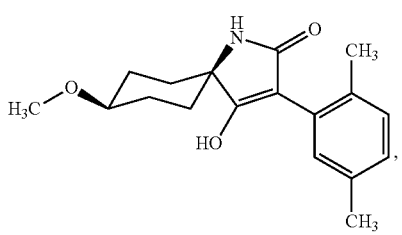
Spirotetramat both compounds known from WO 04/007448, (I-2)
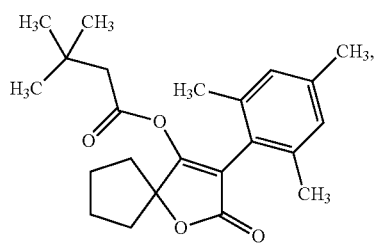
spiromesifen (I-3), or (I-3)
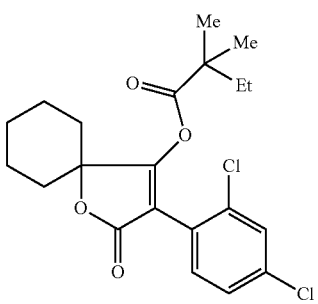 [SMILES: CCC(C)(C)C(=O)OC1=C(c2ccc(Cl)cc2Cl)C(=O)OC12CCCCC2]

spirodiclofen (I-4) known from
and at least one acetylcholine receptor agonist or antagonist, in particular a compound of the following formulae:

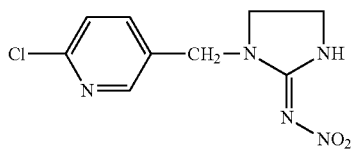 [SMILES: O=[N+]([O-])/N=C1\NCCN1Cc1ccc(Cl)nc1]

imidacloprid (A1), disclosed in EP-A-00192060 and/or

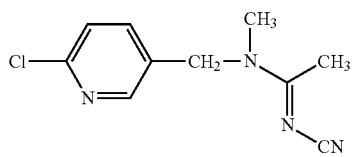

acetamiprid (A2), disclosed in WO 91/04965 and/or

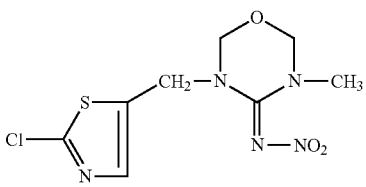 [SMILES: CN1COCN(Cc2cnc(Cl)s2)/C1=N/[N+](=O)[O-]]

thiomethoxam (A3), disclosed in EP-A-00580553 and/or

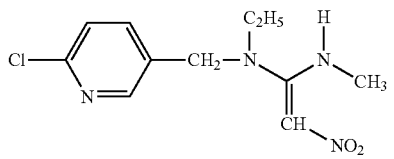

nitenpyram (A4), disclosed in EP-A-00302389 and/or

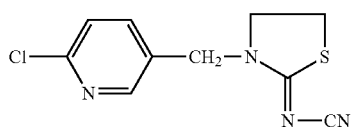 [SMILES: N#C/N=C1\SCCN1Cc1ccc(Cl)nc1]

thiacloprid (A5), disclosed in EP-A-00235725 and/or

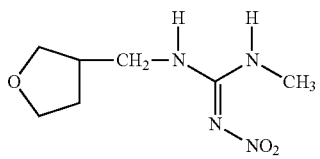

dinotefuran (A6), disclosed in EP-A-00649845
and/or

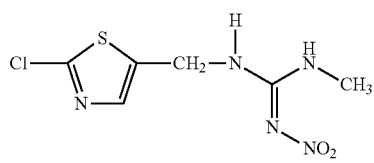

clothianidin (A7), disclosed in EP-A-00376279
and/or

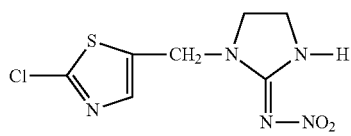

imidaclothiz (A8), disclosed in EP A 00192060. These are known, commercially available compounds.

In an aspect, a combination described herein comprises, consists of, or consists essentially of compounds of the formula (I-1) and at least one active substance from the group of the acetylcholine receptor agonists or antagonists.

In an aspect, a combination described herein comprises, consists of, or consists essentially of compound of the formula (I-2) and at least one active substance from the group of the acetylcholine receptor agonists or antagonists.

In an aspect, a combination described herein comprises, consists of, or consists essentially of compound of the formula (I-3) and at least one active substance from the group of the acetylcholine receptor agonists or antagonists.

In an aspect, a combination described herein comprises, consists of, or consists essentially of compound of the formula (I-4) and at least one active substance from the group of the acetylcholine receptor agonists or antagonists.

The following combinations are examples: (I-1)+(A1), (I-1)+(A2), (I-1)+(A3), (I-1)+(A4), (I-1)+(A5), (I-1)+(A6), (I-1)+(A7), (I-1)+(A8), (I-2)+(A1), (I-2)+(A2), (I-2)+(A3), (I-2)+(A4), (I-2)+(A5), (I-2)+(A6), (I-2)+(A7), (I-2)+(A8), (I-3)+(A1), (I-3)+(A2), (I-3)+(A3), (I-3)+(A4), (I-3)+(A5), (I-3)+(A6), (I-3)+(A7), (I-3)+(A8), (I-4)+(A1), (I-4)+(A2), (I-4)+(A3), (I-4)+(A4), (I-4)+(A5), (I-4)+(A6), (I-4)+(A7), (I-4)+(A8).

In an aspect, a combination described herein comprises, consists of, or consists essentially of the compound of the formula (I-2) and at least one active substance from the group of the acetylcholine receptor agonists or antagonists.

In an aspect, a combination described herein comprises, consists of, or consists essentially of the compound of the formula (I-1) and imidacloprid (A-1).

In an aspect, a combination described herein comprises, consists of, or consists essentially of the compound of the formula (I-3) and imidacloprid (A-1).

In an aspect, a combination described herein comprises, consists of, or consists essentially of, the compound of the formula (I-2) and imidacloprid (A-1).

Surprisingly, it has been found that the insecticidal activity of the active substance combinations according to the invention against animal pests, especially chinch bugs from the Lygaeidae family; and other insects and foliage feeding pests demonstrating resistance to pyrethroids is considerably higher than the sum of the activities of the individual active substances. A true synergistic effect has been found which could not have been predicted exists, not simply a complementation of action.

The weight ratios of the active substances in the active substance combinations may be varied within a relatively wide range. In an aspect, a combination described herein comprise active substances of the formula (I-1), (I-2), (I-3), or (I-4) and (A1)-(A7) in the preferred and especially preferred ratios which are detailed in the table herein below:

the ratios are based on weight ratios. The ratio should be interpreted as active substance of the formula (I-1), (I-2), (I-3), and (I-4):(A1)-(A7)

|  | Mixing or Application ratio | Preferred ratio | Especially preferred ratio | Very preferred ratio |
|---|---|---|---|---|
| Imidacloprid | 50:1 to 1:50 | 25:1 to 1:25 | 5:1 to 1:5 | 3:1 to 1:3 |
| Acetamiprid | 50:1 to 1:50 | 25:1 to 1:25 | 5:1 to 1:5 | 3:1 to 1:3 |
| Thiamethoxam | 50:1 to 1:50 | 25:1 to 1:25 | 5:1 to 1:5 | 3:1 to 1:3 |
| Nitenpyram | 50:1 to 1:50 | 25:1 to 1:25 | 5:1 to 1:5 | 3:1 to 1:3 |
| Thiacloprid | 50:1 to 1:50 | 25:1 to 1:25 | 5:1 to 1:5 | 3:1 to 1:3 |
| Dinotefuran | 50:1 to 1:50 | 25:1 to 1:25 | 5:1 to 1:5 | 3:1 to 1:3 |
| Clothianidin | 50:1 to 1:50 | 25:1 to 1:25 | 5:1 to 1:5 | 3:1 to 1:3 |
| Imidaclothiz | 50:1 to 1:50 | 25:1 to 1:25 | 5:1 to 1:5 | 3:1 to 1:3 |

In an aspect, the nicotinic acetylcholine receptor agonist or antagonist is imidacloprid.

In an aspect, a combination described herein may also comprise further fungicidally, acaricidally or insecticidally actives.

In an aspect, binders, coating agents, wetting agents, or buffering agents can be added to a combination or composition described herein. In another aspect, at least one agriculturally acceptable carrier can be added to the formulation such as water, solids or dry powders. The dry powders can be derived from a variety of materials such as wood barks, calcium carbonate, gypsum, vermiculite, talc, humus, activated charcoal, and various phosphorous compounds. In an aspect, a combination or composition described herein can include a spray or tank mix adjuvant.

Components of a combination or composition described herein can be converted into the customary formulations, such as solutions, emulsions, wettable powders, suspensions, powders, dusts, pastes, soluble powders, granules, suspoemulsion concentrates, natural and synthetic materials impregnated with active substances, and ultrafine encapsulation in polymeric material.

These formulations are produced in a known manner, for example by mixing the active substance with extenders, such as, liquid solvents and/or solid carriers, optionally with the use of surface-active agents, that is, emulsifiers and/or dispersants and/or foam formers.

Suitable extenders are, for example, water, polar and unpolar organic chemical fluids, for example from the classes of the aromatic and nonaromatic hydrocarbons (such as paraffins, alkylbenzenes, alkylnaphthalenes, chlorobenzenes), of the alcohols and polyols (which may optionally also be substituted, etherified and/or esterified), of the ketones (such as acetone, cyclohexanone), esters (also fats and oils) and (poly) ethers, of the unsubstituted and substituted amines, amides, lactams (such as N-allylpyrrolidones) and lactones, of the sulfones and sulfoxides (such as dimethyl sulfoxide).

If water is used as extender, auxiliary solvents which can also be used are, for example, organic solvents. As liquid solvents, there are suitable: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol and ethers and esters thereof, ketones, such as acetone, methyl ethyl ketone, methyl isobutyl ketone or cyclohexanone, strongly polar solvents, such as dimethylformamide and dimethyl sulfoxide, and water.

Solid carriers which are suitable are for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; as emulsifiers and/or foam formers there are suitable: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolysates; as dispersants there are suitable: for example lignosulfite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Further additives may be mineral and vegetable oils.

Colorants can be used, such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

In an aspect, a combination or composition described herein comprise between 0.1 and 95% by weight of active substance. In an aspect, a combination or composition described herein is between 0.5 and 90% of active substance.

In an aspect, a combination described herein is applied to a crop at about 1-1000 grams of ketoenol per hectacre, and about 1-1000 grams of nicotinic acetylcholine receptor agonist or antagonist per hectare. In an aspect, a combination described herein is applied to a crop at about 1-500 grams of ketoenol per hectacre, and about 1-500 grams of nicotinic acetylcholine receptor agonist or antagonist per hectare. In an aspect, a combination described herein is applied to a crop at about 1-250 grams of ketoenol per hectacre, and about 100-500 grams of nicotinic acetylcholine receptor agonist or antagonist per hectare. In an aspect, a combination described herein is applied to a crop at about 100-200 grams of ketoenol per hectacre, and about 200-500 grams of nicotinic acetylcholine receptor agonist or antagonist per hectare. In an aspect, a combination described herein is applied to a crop at about 85-180 grams of ketoenol per hectacre, and about 220-450 grams of nicotinic acetylcholine receptor agonist or antagonist per hectare. In an aspect, a combination described herein is applied to a crop at about 88-176 grams of ketoenol per hectacre, and about 224-448 grams of nicotinic acetylcholine receptor agonist or antagonist per hectare. In an aspect, a combination described herein is applied to a crop at about 176 grams of ketoenol per hectacre, and about 448 grams of nicotinic acetylcholine receptor agonist or antagonist per hectare.

In an aspect, the combination or composition of ketoenol to nicotinic acetylcholine receptor agonist or antagonist described herein is present in a ratio of between 100:1 to 1:100. In an aspect, the combination or composition of ketoenol to nicotinic acetylcholine receptor agonist or antagonist described herein is present in a ratio of between 1:1 to 1:100. In an aspect, the combination or composition of ketoenol to nicotinic acetylcholine receptor agonist or antagonist described herein is present in a ratio of between 1:1 to 1:50. In an aspect, the combination or composition of ketoenol to nicotinic acetylcholine receptor agonist or antagonist described herein is present in a ratio of 1:1 to 1:25. In an aspect, the combination or composition of ketoenol to nicotinic acetylcholine receptor agonist or antagonist described herein is present in a ratio of 1:1 to 1:10. In an aspect, the combination or composition of ketoenol to nicotinic acetylcholine receptor agonist or antagonist described herein is present in a ratio of 1:1 to 1:5. In an aspect, the combination or composition of ketoenol to nicotinic acetylcholine receptor agonist or antagonist described herein is present in a ratio of 1:2.5. Extenders and/or surface-active agents as described above can be added.

The application is effected in a customary manner adapted to suit the use forms, for example, the combination described herein can be applied as a tank mix (imidacloprid+spirotetramat), pre-mixed combination product sold in one bottle to the customer, granular formulation, granular formulation on fertilizer formulation, plant pen, or table form, imidacloprid sprayed first and spirotetramat sprayed next, or vice versa. Applications can be made through irrigation system, hose end sprayer, and ready to use sprayer.

In an aspect, a combination or composition comprising, consisting of, or consisting essentially of nicotinic acetylcholine receptor agonist or antagonist and ketoenol, is applied to turfgrass, in a method described herein. In an aspect a combination or composition comprising, consisting of, or consisting essentially of imidacloprid and spirotetramat is applied to turfgrass in a method described herein.

In an aspect, a combination or composition described herein is applied to turfgrass in a single application step. In another aspect, a combination or composition described herein is applied in multiple application steps to turfgrass. In yet another aspect, a combination or composition described herein is applied in one, two, three or more application steps to turfgrass.

In an aspect, the nicotinic acetylcholine receptor agonist or antagonist and ketoenol are applied at the same time in a single application step or sequentially.

In an aspect, the nicotinic acetylcholine receptor agonist or antagonist and ketoenol are applied individually or mixed and applied at the same time.

In an aspect, the disclosure provides for a method of reducing plant damage caused by animal pests by applying a combination or composition described herein. In an aspect, the disclosure provides a method of controlling animal pests by applying a combination or composition described herein. In an aspect, the disclosure provides for a method of controlling animal pests that have shown resistance to pyrethroids by applying a combination or composition described herein.

In an aspect, the combination or composition described herein can be used to control one or more of the following animal pests, for example, chinch bug (Family Lygaeidae), especially including southern chinch bug, Annual bluegrass weevil (Family Curculionidae), Rhodesgrass mealybug (Family Pseudococcidae), Banks grass mite (Family Tetranychidae), Ground pearls (Family Margarodidae), 2-lined spittlebug (Family Cercopidae), Billbug (Family Curculionidae), in any environment where the pests grow, for example, turfgrasses. Turfgrass include all grasses such as St. Augustine grass, bermudagrass, bahiagrass, buffalograss, centipedegrass, Kentucky bluegrass, fine fescue, tall fescue, perennial ryegrass, creeping bentgrass, zoysiagrass, crabgrass, guineagrass, pangolagrass, torpedograss, and tropical carpetgrass.

In an aspect, the combination or composition and method described herein can be used to control *Blissus* spp. in turfgrass. Examples of turfgrass are St. Augustine grass, bermudagrass, bahiagrass, buffalograss, centipedegrass, Kentucky bluegrass, fine fescue, tall fescue, perennial ryegrass, creeping bentgrass, zoysiagrass, crabgrass, guineagrass, pangolagrass, torpedograss, and tropical carpetgrass.

In an aspect, the combination or composition described herein can be used to control the following species from the chinch bug family (Lygaeidae): *Blissus leucopterus leucopterus, Blissus leucopterus hirtus, Blissus insularis*, and *Blissus occiduus*, in turfgrass In an aspect, the combination or composition described herein can be used to control the following species of annual bluegrass weevil: *Listronotus maculicollis* in turfgrass.

In an aspect, the combination or composition described herein can be used to control the following species, Rhodesgrass mealybug: *Antonina graminis*, in turfgrass.

In an aspect, the combination or composition described herein can be used to control the following species of mites, Banks grass mite: *Oligonychus pratensis*, Bermudagrass mites, *Eriophys cynodiensis*, and clover mite, *Bryobia praetiosa*, in turfgrass.

In an aspect, the combination or composition described herein can be used to control Ground pearls: *Margarodes prieskaensis, Margarodes vitis, Margarodes vredendalensis*, in turfgrass.

In an aspect, the combination or composition described herein can be used to control the 2-lined spittlebug: *Prosapia bicincta*, in turfgrass.

In an aspect, the combination or composition described herein can be used to control the following species of Billbug: *Sphenophorus venatus, S. parvulus, S. vestitus*, and *S. phoenicia*, in turfgrass.

In an aspect, the combination or composition described herein can be used to control animal pests that have shown resistance to pyrethroids by applying a combination or composition described herein to turfgrass or any environment where the animal pests grow.

Examples of turfgrass capable of being treated in the methods described herein include, for instance, all grasses such as St. Augustine grass, bermudagrass, bahiagrass, buffalograss, centipedegrass, Kentucky bluegrass, fine fescue, tall fescue, perennial ryegrass, creeping bentgrass, zoysiagraoss, crabgrass, guineagrass, pangolagrass, torpedograss, and tropical carpetgrass.

The turfgrass or their parts may be treated with the described combinations or compositions by applying the combinations or compositions directly to the turfgrass or turfgrass parts. In another embodiment, turfgrass and turfgrass parts may be treated indirectly, for example, by treating the environment or habitat in which the turfgrass parts are exposed to. Conventional treatment methods may be used to treat the environment or habitat including dipping, spraying, fumigating, chemigating, fogging, scattering, brushing on, shanking or injecting. A synergistic effect in insecticides is present when the activity of the active substance combinations exceeds the sum of the activities of the active substances applied individually. The good insecticidal activity of the active substance combinations according to the invention can be seen from the examples which follow. While the individual active substances show weaknesses in their activity, the combinations show an activity which exceeds a simple additive effect.

The following examples serve to illustrate certain aspects of the disclosure and are not intended to limit the disclosure.

EXAMPLES

Example 1

Plots approximately 6 feet by 10 feet with three replicates and planted with St. Augustine grass are infested with the Southern Chinch Bug (*Blissus insularis*). Using a sprayer (research back pack sprayers), Spirotetramat (MOVENTO 240 SC) on its own, azadirachtin (AZATIN XL) on its own, and a mixture of imidacloprid (MERIT 240 SC) and azadirachtin, are applied at the application rates specified. The water application rate is 40 gallons per acre. The evaluation is performed 0 days, 4 days, 7 days, and 18 days after the treatment by determining the number of live Southern Chinch Bugs.

TABLE 1

| | | Number of chinch bugs | | | |
|---|---|---|---|---|---|
| Substance | Application Rate | Number of Chinch bugs 0 Days After Application | Number of Chinch bugs 4 Days After Application | Number of chinch bugs 7 Days After Application | Number of chinch bugs 18 Days After Application |
| Untreated | | 4 | 8 | 8 | 7 |
| Spirotetramat | 111 grams/hectare | 6 | 12 | 6 | 10 |
| Azadirachtin | 222 grams/hectare | 12 | 15 | 5 | 11 |
| Imidacloprid + azadirachtin | 111 + 222 grams/hectare | 16 | 12 | 5 | 8 |

As can be seen from Table 1, none of the compounds provided good control of Southern Chinch bugs as the number of chinch bugs either increased or only slightly reduced after treatment with each of the substances, including spirotetramat and imidacloprid alone.

Example 2

Plots approximately 30 ft by 10 ft with 3 replicates and planted with St. Augustine grass are infected with Southern chinch bug (*Blissus insularis*). Using a pneumatic sprayer, a mixture of the spirotetramat (MOVENTO 240 SC) and imidacloprid (MERIT 240 SC) is applied in comparision to the spirotetramat (MOVENTO 240 SC) on its own, the imidacloprid (MERIT 240 SC) on its own, and the gold standard Pyrethrin treatment ALLECTUS™ (imidacloprid+bifenthrin), at the application rates specified. The water application rate is 40 gallons per acre. The evaluation is performed 0 days, 5 days, 13 days, 29 days, 41 days, and 58 days after the treatment by determining the number of chinch bugs and the chlorophyll content of the grass. The higher the chlorophyll content of the grass, the greener and lusher the grass is.

TABLE 2

Number of chinch bugs

| | Application Rate | Number of chinch bugs at 0 Days | Number of chinch bugs at 5 days | Number of chinch bugs at 13 days | Number of chinch bugs at 29 days | Number of chinch bugs at 41 days | Number of chinch bugs at 58 days |
|---|---|---|---|---|---|---|---|
| Untreated | | 50 | 47 | 100 | 43 | 58 | 38 |
| Allectus ™ | 1083 g ai/ha total (309 g ai/ha bifentrin + 773.6 g ai/ha imidacloprid) | 50 | 5 | 10 | 0 | 2 | 1 |
| Imidacloprid | 448.8 g ai/ha | 50 | 19 | 41 | 30 | 65 | 9 |
| Spirotetramat | 175.8 g ai/ha | 50 | 45 | 73 | 45 | 83 | 26 |
| Spirotetramat + Imidacloprid | 175.8 + 448.8 g ai/ha | 50 | 11 | 5 | 7 | 11 | 3 |

TABLE 3

Chlorophyll Content

| | Application Rate | 5 days | 13 days | 41 days | 58 days |
|---|---|---|---|---|---|
| Untreated | | 2.409 | 2.101 | 1.802 | 2.114 |
| Allectus ™ | 1083 g ai/ha total (309 g ai/ha bifentrin + 773.6 g ai/ha imidacloprid | 2.877 | 3.202 | 4.283 | 3.682 |
| Imidacloprid | 448.8 g ai/ha | 2.733 | 3.215 | 3.185 | 3.250 |
| Spirotetramat | 175.8 g ai/ha | 3.338 | 3.250 | 2.292 | 2.149 |
| Spirotetramat + Imidacloprid | 175.8 + 448.8 g ai/ha | 3.031 | 3.158 | 3.951 | 3.660 |

As can be seen from Table 2, neither spirotetramat or imidacloprid alone provided good control of Southern chinch bugs, as the number of Southern chinch bugs either increased or only slightly reduced after treatment. However, a mixture of spirotetramat and imidacloprid provides very good control of Southern chinch bugs, as the number of Southern chinch bugs decreased dramatically in the days after treatment, and stayed controlled even at 58 days after treatment. These results are comparable to that of the standard treatment, Allectus™.

As can be seen from Table 3, the chlorophyll content of turfgrass treated with imidacloprid and spirotetramat alone is similar to that of the untreated turfgrass. However, the cholorophyll content of the turfgrass treated with a mixture of imidacloprid and spirotetramat, especially further out after treatment (41 days and 58 days after treatment), is higher than that of imidacloprid or spirotetramat alone, and is comparable to the chlorophyll content of the gold standard treatment, Allectus™.

The invention claimed is:

1. A method for treating turf grass infected with Southern Chinch bugs, comprising applying to the turfgrass imidacloprid and spirotetramat, wherein the spirotetramat and imidacloprid are applied in a ratio of between 1:1 to 1:25.

2. A method according to claim 1, wherein the Chinch bugs have shown resistance to pyrethroids.

3. A method according to claim 1, wherein the turfgrass is St. Augustine grass, bermudagrass, bahiagrass, buffalograss, centipedegrass, Kentucky bluegrass, fine fescue, tall fescue, perennial ryegrass, creeping bentgrass, zoysiagraoss, crabgrass, guineagrass, pangolagrass, torpedograss, or tropical carpetgrass.

4. The method according to claim 1, wherein the turfgrass is St. Augustine Grass.

5. The method according to claim 1, wherein the spirotetramat is applied at an application rate of about 1 to 250 grams of active ingredient per hectare and the imidacloprid is applied at an application rate of about 200 to 500 grams active ingredient per hectare.

6. The method according to claim 1, wherein the spirotetramat and the imidacloprid are applied together.

7. The method according to claim 1, wherein the spirotetramat and the imidacloprid are applied sequentially.

8. The method according to claim 1, wherein the spirotetramat and imidacloprid are applied in a ratio of between 1:1 to 1:5.

9. The method according to claim 5, wherein the spirotetramat is applied at an application rate of about 100 to 200 grams of active ingredient per hectare.

* * * * *